United States Patent [19]

Strock

[11] Patent Number: 4,641,641

[45] Date of Patent: Feb. 10, 1987

[54] PROTECTIVE APPLIANCE FOR THE HIP JOINT AREA

[76] Inventor: Alvin E. Strock, 647 Commonwealth Ave., Newton Centre, Mass. 02159

[21] Appl. No.: 775,819

[22] Filed: Sep. 13, 1985

[51] Int. Cl.$^4$ ............................................. A61F 13/00
[52] U.S. Cl. ........................................ 128/132 R; 2/2
[58] Field of Search ............ 2/2 R, 22; 128/82, 132 R

[56] References Cited

U.S. PATENT DOCUMENTS 3,526,221  9/1970  Garber ........................... 128/132 R
4,573,216  3/1986  Wortberg .................................. 2/2

FOREIGN PATENT DOCUMENTS 2082919  3/1982  United Kingdom ............ 128/132 R

*Primary Examiner*—Stephen F. Husar

*Attorney, Agent, or Firm*—Thomas C. O'Konski

[57] ABSTRACT

A protective appliance for the hip joint area comprises an annular pad made of a relatively resilient material and carrying adhesive strips on one surface to secure the pad to the skin, and a relatively rigid dome-shaped shield carried in opposed pockets formed on the other, outer surface of the pad. When the appliance is in place, the shield serves to disperse forces directed toward the hip joint area, transferring such forces to surrounding regions which are inherently better protected by body tissue. The shield fits somewhat loosely in the pad pockets to permit it to adjust to changes in body position, thus adding to the comfort of the appliance when it is worn. The sides of the shield disposed between the pad pockets are contoured out of the plane of the pad to add further comfort particularly when the wearer reclines on the appliance.

15 Claims, 5 Drawing Figures

PROTECTIVE APPLIANCE FOR THE HIP JOINT AREA

BACKGROUND OF THE INVENTION

This invention relates to a protective appliance for the hip joint area, and more particularly, to a protective appliance which may be worn comfortably on the body and which will disperse forces directed toward the hip joint area, transferring such forces away from the particularly vulnerable regions of the hip to surrounding regions which are inherently protected by body tissue.

There are over 200,000 hip fractures suffered by humans each year plus uncounted numbers of other hip joint injuries which result in pain, disruption of normal life and substantial medical cost. These fractures and other injuries are particularly common in elderly people, who experience degenerative changes in bone and tissue structure with advancing age. Given over every increasing life expectancies, the number of these injuries and the costs associated with them can only increase with time.

The hip joint is an enarthrodial or ball-and-socket joint, formed by the reception of the ball-shaped head on the upper or proximal end of the femur into the cup-shaped cavity in the pelvis called the acetabulum. A fall or blow to the hip joint area, if it is unprotected, can result in body tissue injuries, in dislocation of the femur head from the acetabulum, and/or in fractures of the acetabulum or various parts of the proximal femur. Particularly vulnerable is the so-called greater trochanter which protrudes outwardly from the proximal femur just below the joint. This region is relatively poorly protected by muscle and other body tissue in comparison with the regions of the hip which surround it. In fact, the greater trochanter is readily accessible to the touch, its position being generally indicated by a depression in the hip area, owing to the thickness of the muscles which cover the bone and protrude above and below it.

There have been a variety of appliances proposed by others heretofore intended to be worn over the hip joint area and to protect that area from potentially damaging forces. However, none of these appliances has experienced widespread acceptance or use. The primary problem is that the prior appliances which are capable of providing adequate protection are generally difficult to apply and uncomfortable to wear. An effective hip joint area protective appliance has simply not been available which is sufficiently comfortable to wear for extended periods of time, including through normal day-time activites as well as in sleeping at night.

Accordingly, it is a primary object of the present invention is to provide a protective appliance which serves to reduce the likelihood of fracture or other injury to the hip joint area.

Another object of this invention is to provide a protective appliance which can be applied to and removed from the skin about the hip joint area with relative ease and without the need of straps, bandages or other devices that are difficult to manipulate and apply.

Another object of this invention is to provide a protective appliance for the hip joint area which is both small and lightweight, making it comfortable to wear for extended periods of time.

Another object of this invention is to provide a protective appliance for the hip joint area which is capable of adjusting to changes in body position when worn, thereby adding to its comfort particularly while the wearer is active.

Another object of this invention is to provide a protective appliance for the hip joint area which is designed to be relatively unobtrusive and comfortable even when the wearer reclines on it, as when sleeping.

Another object of this invention is to provide a protective appliance for the hip joint area which permits the skin to maintain some direct contact with the atmosphere and water to flow through it when bathing and the like, as well as visual inspection of portions of the hip joint area without removal of the appliance.

Still another object of this invention is to provide a protective appliance for the hip joint area which comprises a relatively rigid shield and a relatively flexible support pad that can be separated from one another so that each can be cleaned or replaced independently of the other.

Other objects will be described in or made apparent from the detailed description below.

To accomplish these and other objects, a protective appliance for the hip joint area embodied in accordance with the present invention comprises two parts: a pad made of a relatively flexible and soft material, and a shield made of a relatively rigid material and removably carried by the pad. One surface of the pad is provided with adhesive strips permitting it to be securd to the skin at the hip joint area, preferably directly over the region of the greater trochanter. The shield is generally dome-shaped with counter-extending flanges that extend into opposing pockets formed on the other, outer surface of the pad. The dome shape of the shield causes it to disperse forces directed toward the hip joint area, transferring them to the regions of the hip area which surround the greater trochanter and which are inherently better protected by body tissue. The shield fits somewhat loosely in the pad pockets, permitting it to shift somewhat and adjust to changes in body position when it is worn, adding considerably to its comfort. The sides of the shield between its two flanges are contoured outwardly away from the plane of the pad so as to add further comfort, particularly when the wearer of the appliance reclines on it, as when sleeping or the like.

In the preferred embodiment of the invention described in detail below, the pad is annular in shape and the shield is made of a clear plastic material. The resulting hole in the pad permits the exposed skin to maintain direct contact with the atmosphere and water to flow through the appliance during bathing and the like when falls or other damaging blows to the hip are common. The hole and clear shield also aid in properly locating the appliance on the hip, and permit visual inspection of the exposed hip area with the appliance secured in place.

These and other objects, features and advantages of the invention will be better understood and appreciated from the following detailed description of an actual embodiment thereof, selected for purposes of illustration only and shown specifically in the accompanying drawing.

DETAILED DESCRIPTION OF THE PREFERRED EMBODIMENTS

Figure 1:
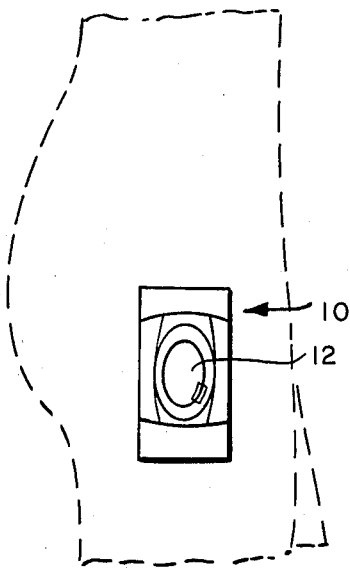
FIG. 1 is a perspective view of a protective appliance embodied in accordance with this invention shown positioned on the hip of a human subject suggested in broken lines.

Referring now specifically to the drawing, and initially to FIG. 1 thereof, there is shown a hip joint area protective appliance embodying the present invention mounted on the hip of a human subject. The appliance basically comprises two parts: a pad 10 and a shield 12. Typically, the pad 10 may be about 3 by 6 inches in plan, and the overall height of the appliance measured from the outer surface of the shield 12 to the inner surface 16 of the pad 10 may be approximately one inch. Those dimensions may, of course, vary. Smaller sizes would be suitable for use by children, infants and the like.

As indicated in FIG. 1, the appliance is intended to be secured on the hip so that the shield 12 is centered over the region of the greater trochanter, whose position is generally indicated by a depression in the hip created by the relatively large and thick muscles which cover the bone in that area and protrude above and below it. The position of the greater trochanter is generally easy to locate by a simple tactile examination of the hip.

Figure 2:
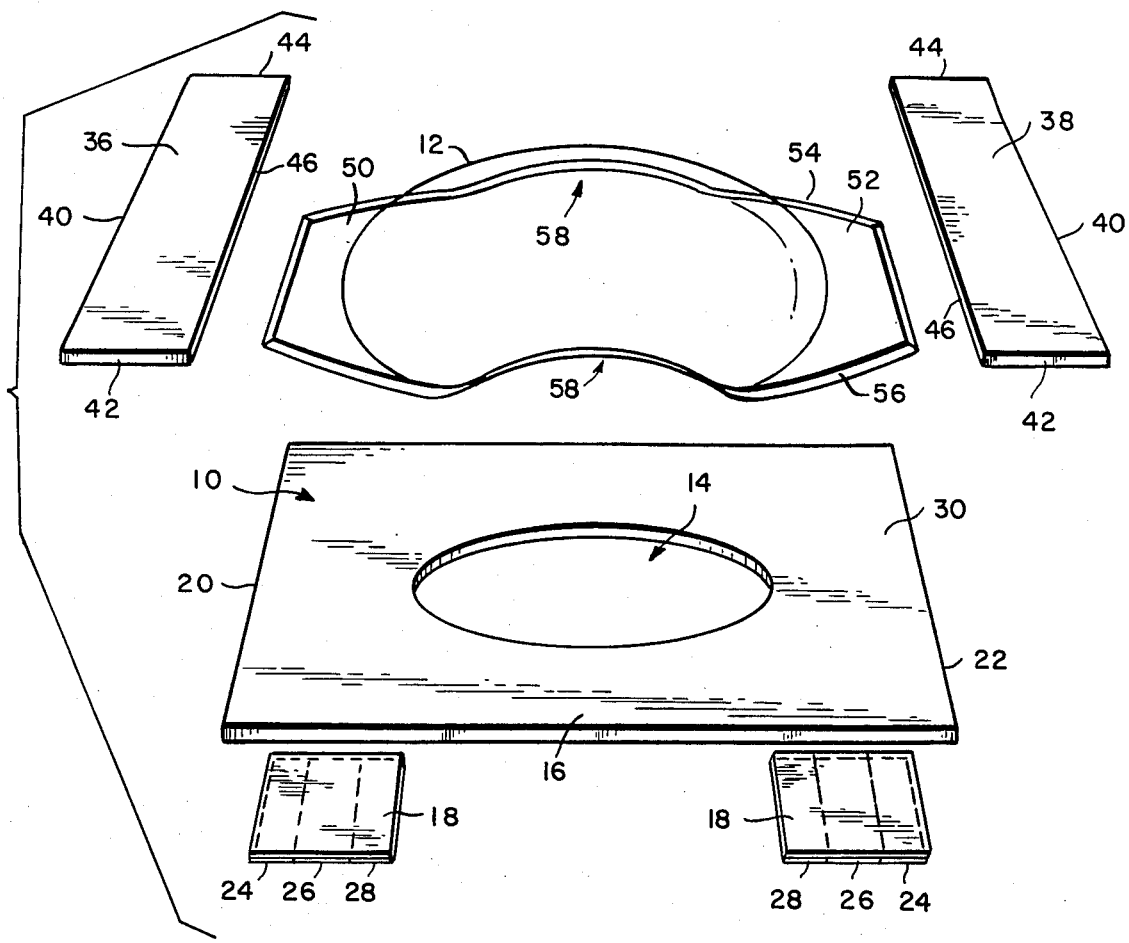
FIG. 2 is an exploded view of the appliance of FIG. 1 showing its various parts.

The pad 10 is preferably made of a closed cell polyethylene foam having a density of approximately 6 pounds per cubic foot. As indicated in FIG. 2, the pad 10 is provided with an elliptical cut-out 14 whose long dimension is coincident with the long center line of the pad 10. Cut-out 14 is sufficiently large to expose the region of the greater trochanter of the person wearing the appliance. As explained in more detail below, this facilitates proper placement of the appliance and also permits air contact and water to flow through to the skin when the appliance is worn during bathing and the like.

To secure the pad 10 to the skin, the inner surface 16 of the pad carries a pair of spaced apart tabs 18 of adhesive adjacent the respective end edges 20 and 22 of the pad at opposite ends of the cut-out 14. Each adhesive tab 18 is protected by a removable covering, preferably in the form of three separate strips 24, 26 and 28. Removal of the strips 24, 26 and 28 exposes the adhesive tabs 18. Localized tabs 18 of adhesive are used in lieu of covering the entire inner surface 16 of the pad 10 with adhesive, since such adhesive localization reduces pulling of the skin due to body movement when the appliance is worn, and thus adds to its comfort. The separate strips 24, 26 and 28 allow the wearer to select the amount of adhesive that is to be exposed, depending, for example, upon the length of time the appliance is to be worn, with typically larger areas of adhesive being exposed for longer expected wearing periods. Alternatively, the strips 24, 26 and 28 allow the appliance to be applied, then removed and applied again, by exposing a fresh area of the adhesive tabs 18 prior to the re-application.

The outer surface 30 of the pad 10 is provided with a pair of pockets 32 and 34 (FIG. 4) beyond the extreme ends of the cut-out 14. The pockets 32 and 34 face one another and are adapted to receive counter-extending flanges 50 and 52 formed as an integral part of the shield 12. The pockets are formed by thin padded strips 36 and 38 that are suitably secured to the surface 30 of the pad 10 along sides 40, 42, and 44 of the strips 36 and 38. Access to the pockets 32 and 34 is provided beneath the unsecured sides 46 of the strips 36 and 38 which lie adjacent the ends of the cut-out 14.

Figure 3:
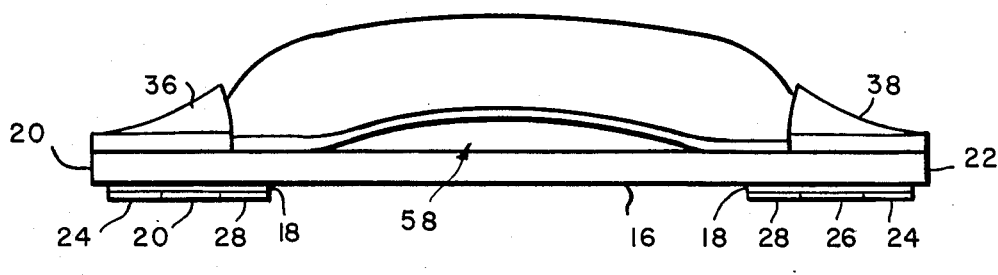
FIG. 3 is a side view of the assembled appliance of FIGS. 1 and 2.
Figure 4:
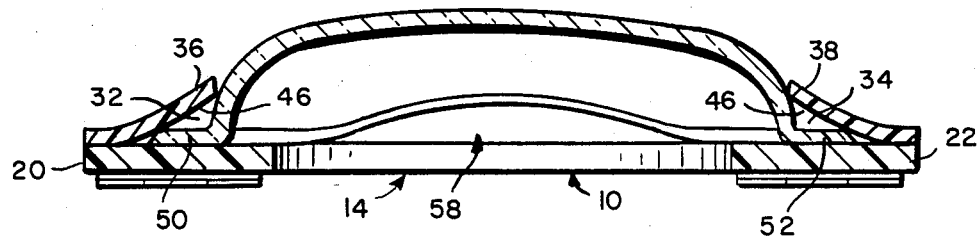
FIG. 4 is a vertical cross sectional view of the appliance.
Figure 5:
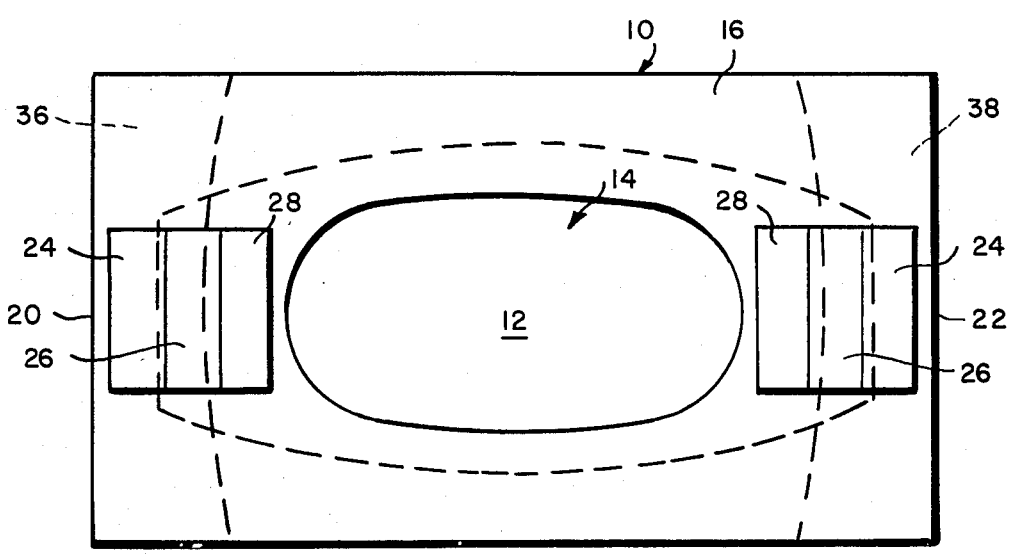
FIG. 5 is a bottom plan view of the same.

The shield 12 is generally elliptical in plan and is dome-shaped when viewed from the side as shown in FIGS. 3 and 4. The shield 12 is made of a relatively rigid, impact resistant material that is illustratively transparent, such as the clear polycarbonate plastic marketed under the trademark LEXAN, or other comparable substitute. The main body of the shield 12 is dome-shaped so as to extend above the outer surface 30 of the pad. The flanges 50 and 52 formed at the opposite ends of the shield 12 are coplanar so as to present a substantially flat surface of relatively large area against the outer surface 30 of the pad 10. The width of the flanges diminish uniformly away from the domed portion of the shield, and the edges are smooth so as to be free of sharp corners. In its preferred form, the shield 12 is molded to the desired shape and has a stock thickness of approximately $\frac{1}{8}$ inch.

This shape and configuration causes the shield 12 to disperse forces directed toward the hip joint area, particularly those directed at the relatively vulnerable greater trochanter region, transferring them to the surrounding regions which, as noted above, are inherently better protected by body tissue. The relatively large area of the shield flanges 50 and 52 cushions the effect of these forces on the hip area. The resiliency of the pad 10 provides further cushioning in this respect.

As suggested above, the flanges 50 and 52 of the shield 12 fit somewhat loosely in the pockets 32 and 34 so that limited movement of the shield is permitted on the pad 10, generally angularly about an axis normal to the plane of the pad and centered in the cut-out 14. Therefore, as the body of the wearer moves, for example, when changing from a standing to a setting position or vice versa, the shield 12 is permitted to shift angularly and to find its most suitable position depending upon the relative orientation of the wearer's legs. This ability to adjust to body movement adds considerably to the comfort of the appliance, particularly for active wearers. At the same time, the slight angular movements made by the shield in so adjusting to body movements do not diminish the protection afforded by the appliance, since the dome of the shield remains in each case generally centered over the most vulnerable region of the hip joint area.

The edges 54 and 56 of the shield 12 between the flanges 50 and 52 are contoured outwardly away from the plane of the flanges so as to provide a substantial contoured gap 58 between the shield and the pad 10 along each side of the shield 12. These gaps 58 also add considerably to the comfort of the appliance, particularly when the wearer reclines upon it as when sleeping or the like. Specifically, because of these gaps 58, the side edges of the relatively rigid shield 12 are not forced against the pad 10 under the body weight of the wearer during reclining. There are thus no relatively sharp edges of relatively rigid material to press inwardly against the wearer's hip area as he or she rolls over or reclines with the appliance secured in place.

The pockets 32 and 34 which releasably hold the flanges 50 and 52 allow the easy removal of the shield 12, and the pad 10 itself may be replaced when it becomes soiled or when the several adhesive tabs 18 lose their effectiveness, or for any other reason.

Preferably, the adhesive tabs 18 on the inner surface 16 of the pad 10 are formed of a hypo-allogenic adhesive so as to minimize the likelihood of skin irritation caused by the appliance. The pad 10 itself is preferably made of a waterproof material to permit the appliance to be worn during bathing and the like. In this respect, the contoured gaps 58 in the sides of the shield 12 and the cut-out 14 at the center of the pad 10 allow the skin exposed thereby to maintain direct contact with the atmosphere and water to flow through to the hip joint area thus making it unnecessary to remove the appliance during bathing and the like when falls and other blows to the hip joint area are common.

As noted earlier, the cut-out 14 in the pad 10 is also an aid in the proper placement of the appliance on the hip. One useful method of application is to locate the region of the greater trochanter by tactile examination of the hip, and to place small mark on the skin directly over that region. The pad 10 may then in turn be placed over the area with the mark appearing at the center of the cut-out 14. Thereafter, the shield 12 may be mounted on the pad by slipping its flanges 50 and 52 into the pockets 32 and 34. Obviously, if the shield 12 is made of a transparent material, the appliance can be mounted with the shield already in place in the pockets 32 and 34 using the mark applied to the skin as a guide in the placement.

Having described this invention in detail, those skilled in the art will appreciate that many modifications may be made thereof without departing from the spirit of this invention. For example, while the shield 12 is described as being relatively rigid, it could also be made of a material, such as hard rubber or the like, which has some degree of flexibility. It is sufficient for purposes of the invention that the shield 12 have sufficient rigidity to absorb and disperse forces directed against the hip joint area. The shield 12 could also be formed integrally with the pad 10, or removably secured to the pad 10 by a suitable pressure sensitive adhesive or the like, instead of by use of pockets 32 and 34. Additionally, the pad 10 could also be made in a generally ellipitical shape with narrower ends that its middle. Other such modifications will be apparent. Therefore, it is not intended to limit the breadth of this invention to the single embodiment illustrated and described in detail above. Rather, it is intended that the scope of this invention be determined by the appended claims and their equivalents.

What is claimed is:

1. A protective appliance for the hip joint area comprising:
   a pad made of a relatively resilient material adapted to be secured over the hip joint area of a wearer, and having inner and outer surfaces,
   means for securing said pad so that its inner surface overlies the hip joint area of the wearer,
   and a relatively rigid generally dome-shaped shield releasably secured to the outer surface of said pad so as to have portions spaced from the outer surface of said pad, said shield being adapted to disperse forces applied thereto, transferring such forces to portions of the shield contacting pad and surrounding the hip joint area.

2. A protective appliance as described in claim 1 in which said portions of said shield contacting said pad comprise relatively flat flanges lying in face to face contact with the outer surface of said pad, and in which said pad includes spaced apart, oppositely facing pockets on the outer surface of said pad for releasably receiving said flanges of said shield.

3. A protective appliance as described in claim 2 in which said shield flanges fit somewhat loosely within said pockets in said pad, permitting said shield to shift relative to said pad during movement of the hip joint.

4. A protective appliance as described in claim 2 in which said shield has sides that extend between the flanges which are contoured above the outer surface of said pad when the flanges are disposed in said pockets.

5. A protective appliance as described in claim 1 in which said securing means comprises a plurality of parallel adhesive strips secured to the inner surface of said pad and being capable of acting in pairs of spaced apart strips for adhering the appliance to the skin.

6. A protective appliance as described in claim 1 in which said pad has an opening therein at its approximate center.

7. A protective appliance as described in claim 2 in which said pad and said shield are elongated vertically and said flanges and said pockets lie spaced apart at top and bottom ends of said shield and said pad, respectively.

8. A protective appliance for the hip joint area comprising:
   a generally flat pad made of a relatively flexible material having inner and outer surfaces,
   adhesive means for securing the inner surface of said pad to the skin over the area of the hip joint,
   a pair of spaced apart pockets facing one another on the outer surface of said pad,
   and a relatively rigid, generally dome-shaped shield having a pair of oppositely extending flanges releasably captured within the pockets,
   said shield being adapted to disperse forces applied to the appliance, transferring such forces to the portion of said pad in contact with said flanges.

9. A protective appliance as described in claim 8 in which said shield flanges fit somewhat loosely within said pockets in said pad, permitting said shield to shift relative to said pad during movement of the hip joint.

10. A protective appliance as described in claim 8 in which said shield has sides extending between said flanges, said sides being contoured outwardly away from the outer surface of said pad so as to leave contoured gaps between said sides and said pad.

11. A protective appliance as described in claim 8 in which said adhesive means comprises a plurality of adhesive tabs formed on the inner surface of said pad, said tabs being of an area that is less than the area of the inner surface of said pad.

12. A protective appliance as described in claim 11 in which said adhesive tabs are spaced apart from one another on opposite ends of the inner surface of said pad.

13. A protective appliance as described in claim 11 including a covering removably secured over said adhesive tabs, said covering being in a plurality of separate strips each of which is individually removable to expose different areas of said tabs.

14. A protective appliance as described in claim 8 in which said pad defines a through opening at its approximate center.

15. A protective appliance as described in claim 14 in which said shield is formed of a transparent material.

* * * * *